United States Patent
Van Langenhove et al.

(10) Patent No.: US 7,288,244 B2
(45) Date of Patent: Oct. 30, 2007

(54) DETERMINING VULNERABLE PLAQUE IN BLOOD VESSELS

(75) Inventors: Glenn Van Langenhove, Merelbeke (BE); Leonidas Diamantopoulos, Merelbeke (BE)

(73) Assignee: NV Thermocore Medical Systems SA, Merelbeke (BE)

( * ) Notice: Subject to any disclaimer, the term of this patent is extended or adjusted under 35 U.S.C. 154(b) by 583 days.

(21) Appl. No.: 10/323,592

(22) Filed: Dec. 17, 2002

(65) Prior Publication Data

US 2004/0006277 A1    Jan. 8, 2004

Related U.S. Application Data

(63) Continuation-in-part of application No. 10/169,523, filed on Oct. 15, 2002, and a continuation-in-part of application No. 10/188,349, filed on Jul. 2, 2002, now Pat. No. 7,090,645.

(51) Int. Cl.
*A61K 49/00*    (2006.01)

(52) U.S. Cl. ............. 424/9.1; 424/1.11; 424/1.65; 424/9.2; 424/9.3; 424/9.4; 424/9.5; 424/9.6

(58) Field of Classification Search ............ 424/1.11, 424/1.65, 9.1, 9.2, 9.3, 9.4, 9.5, 9.6, 9.7, 424/9.8; 600/549

See application file for complete search history.

(56) References Cited

U.S. PATENT DOCUMENTS

| | | | |
|---|---|---|---|
| 3,589,360 A | 6/1971 | Sinclair | 128/2.05 F |
| 5,237,996 A | 8/1993 | Waldman et al. | 128/642 |
| 5,345,938 A | 9/1994 | Nishiki et al. | 128/660.04 |
| 5,771,895 A | 6/1998 | Slager | 128/662.06 |
| 5,935,075 A * | 8/1999 | Casscells et al. | |
| 5,967,984 A | 10/1999 | Chu et al. | 600/439 |
| 6,053,937 A | 4/2000 | Edwards et al. | 607/104 |
| 6,245,026 B1 | 6/2001 | Campbell et al. | 600/549 |
| 6,763,261 B2 * | 7/2004 | Casscells et al. | 600/549 |

OTHER PUBLICATIONS

Nakano et al (J. Nippon Med. Sch., 2001, 68(6), 482-489).*
WO/01/74263.*

* cited by examiner

*Primary Examiner*—D. L. Jones
(74) *Attorney, Agent, or Firm*—Bromberg & Sunstein LLP

(57) ABSTRACT

The invention is based on the realisation that inflamed plaques in blood vessel walls, which are potentially vulnerable to rupture, can be detected at elevated temperatures which are lower than previously realised. In particular, the low temperatures at which inflamed plaque can be detected are often associated with systems in which blood flow is generally close to normal in particular temperature differences above zero but not more than 0.39° C. have been found to be indicative of the presence of inflamed plaque.

4 Claims, 8 Drawing Sheets

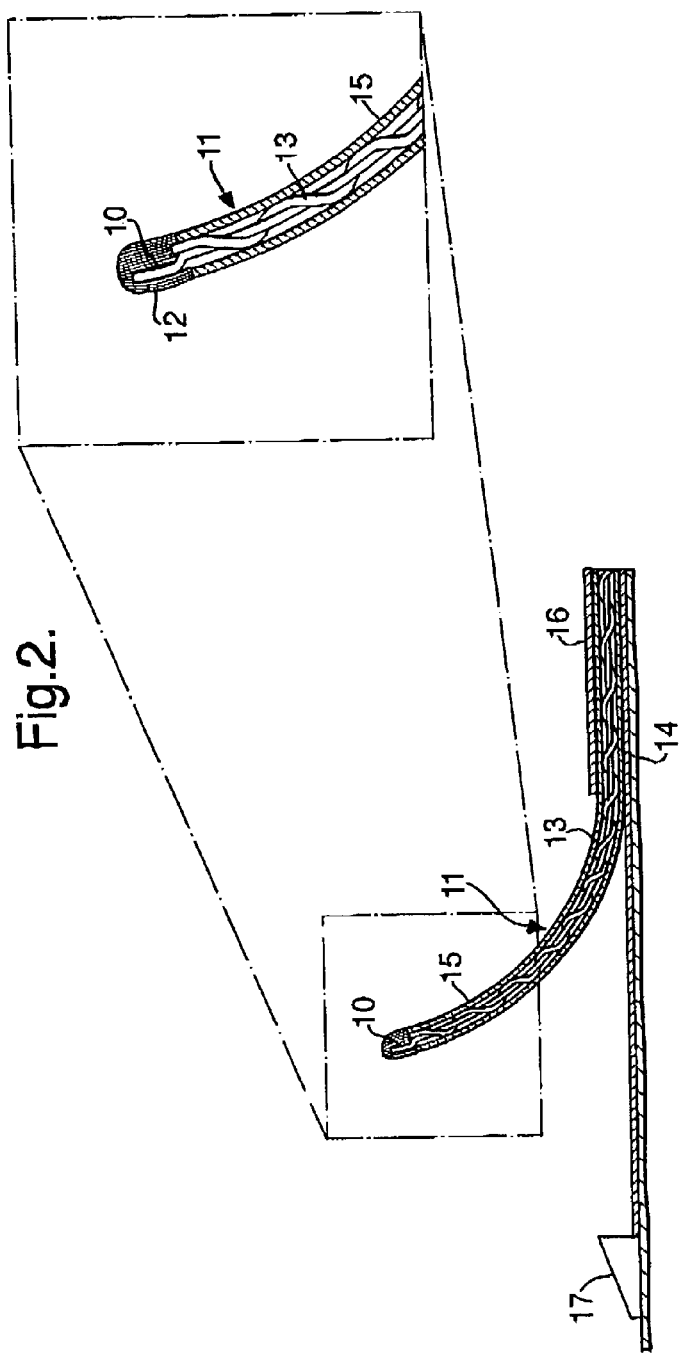
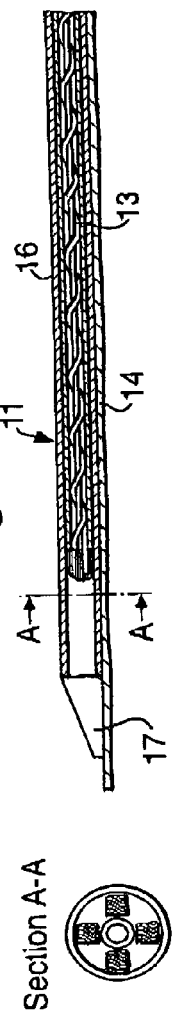

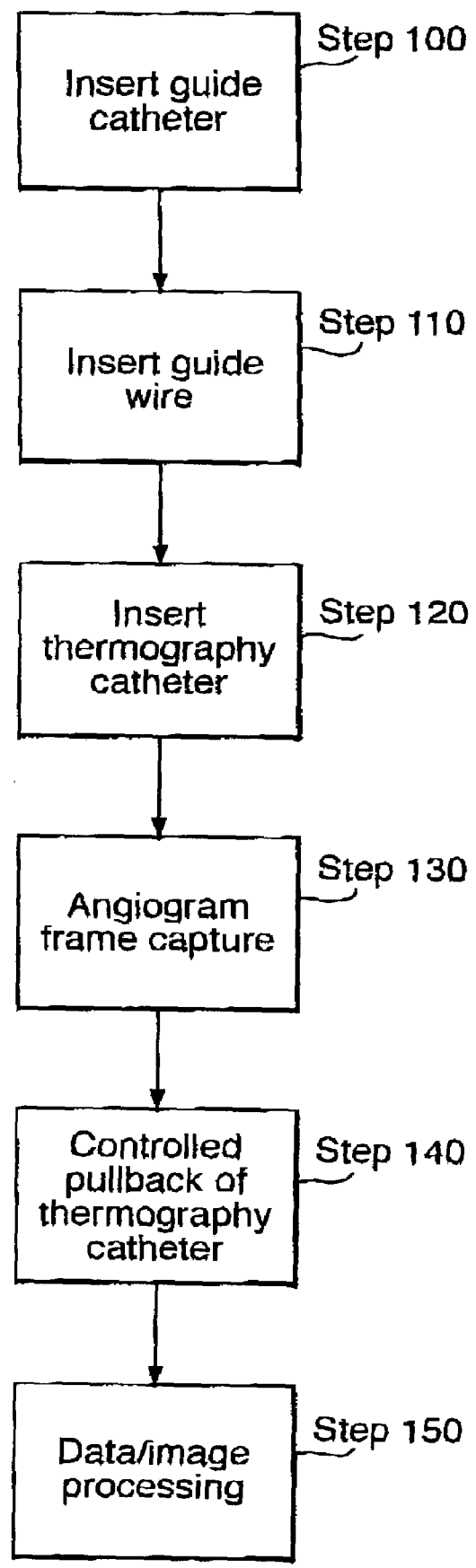

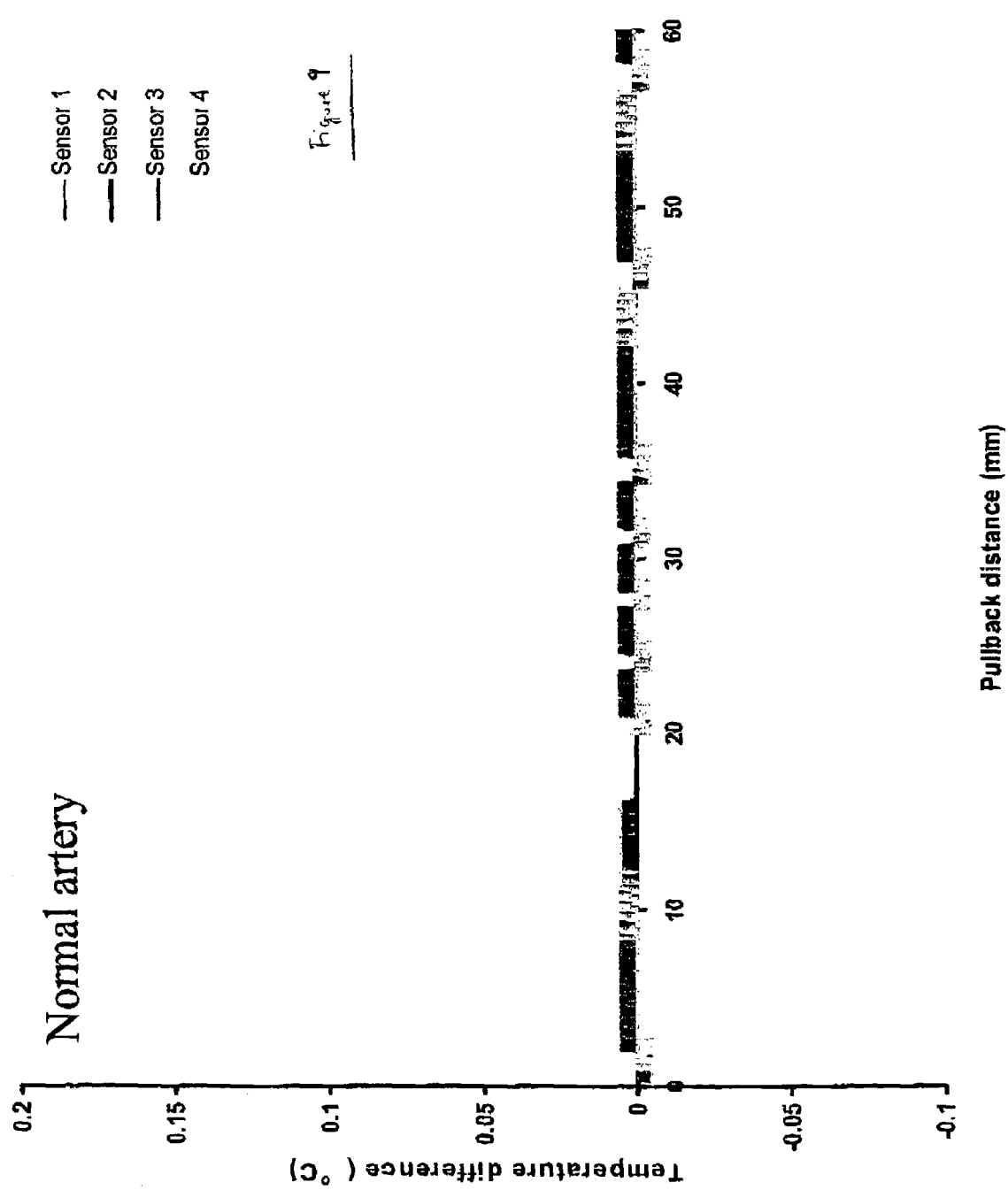

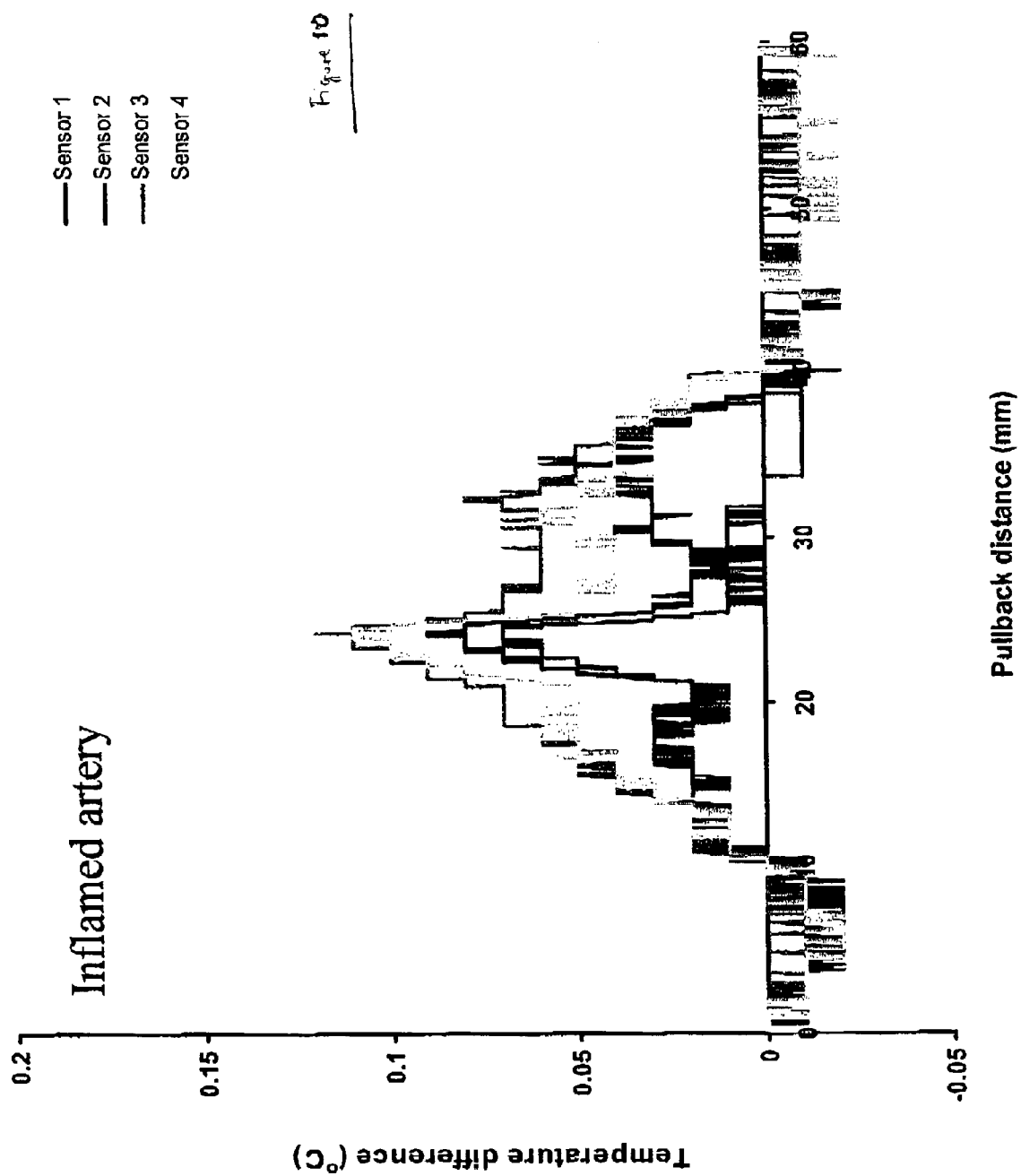

DETERMINING VULNERABLE PLAQUE IN BLOOD VESSELS

CROSS-REFERENCE TO RELATED APPLICATION

The present application is a continuation-in-part of applications Ser. No. 10/169,523 filed 15 Oct. 2002 and entitled "Vascular temperature measuring device and process for measuring vascular temperature", which is a U.S. national phase application of PCT/EP01/04401 with an international filing date of 4 Apr. 2001. This application is also a continuation-in-part of Ser. No. 10/188,349 filed 2 Jul. 2002 now U.S. Pat. No. 7,090,645 and entitled "A biased vascular temperature measuring device."

FIELD OF THE INVENTION

This invention relates to methods of determining whether a subject is at risk of rupture of vulnerable atherosclerotic plaque in one or more blood vessels, or requires further investigation to assess whether there is such a risk, including diagnosing the presence and location of vulnerable atherosclerotic plaque.

BACKGROUND TO THE INVENTION

Plaque can develop in a patient's cardiovascular system The plaque can be quite extensive and occlude a substantial length of the vessel. Additionally, the plaque may be inflamed and unstable, such plaque being subject to rupture, erosion or ulceration which can cause the patient to experience a myocardial infarction, thrombosis or other traumatic and unwanted effects. Such inflamed and unstable plaques are commonly known as vulnerable atherosclerotic plaques. Furthermore, relative blood viscosity rises and aggregation of platelets increases with temperature increases (Dintefass L. Rheology of Blood in Diagnostic and Preventive Medicine London, UK: Butterworths; 1976;66-74).

Previous ex vivo studies have shown that there is indeed thermal heterogeneity in human carotid atherosclerotic plaques (Casscells W, Hawthorn B, David M, Krabach T, Vaughn W K, McAllister H A, Beaman G, Willerson J T. "Thermal detection of cellular infiltrates in living atherosclerotic plaques: possible implications for plaque rupture and thrombosis. Lancet". 1996,347:1447-1449)

Casscells et al postulate that plaque rupture may be predicted by the heat released by activated macrophages which they suggest are either on the plaque surface or under a thin cap. They postulate that measurement of plaque temperature in vivo could be used to identify plaque at increased risk of rupture In particular they note that 37% of the plaques tested by them had "substantially warmer" regions Such regions are described as being 0.4 to 2.2° C. warmer This work is discussed further in U.S. Pat. No. 5,935,075, which again discusses the tact that 37% of the plaques had 1 to 5 substantially warmer (0.4 to 2.2° C.) regions per plaque. It is specifically postulated that the temperatures of plaques which are in danger of rupturing will vary from those less at risk by at least 1.5° C.

The work of Casscells et al was carried out on samples of carotid arteries taken at endarterectomy, in the living state but nevertheless not in the subjects. Measurements in the Casscells et al Lancet paper were carried out using a thermistor (Cole-Parmer model 8402-20) with a 24-gauge needle tip and in addition with a Jet Propulsion Laboratory platinum silicide camera. In U.S. Pat. No. 5,935,075 measurements were made by infrared-sensing, in particular with the use of catheters. The methods used comprise placing an optical fibre capable of transmitting radiation proximate to the position at which temperature is to be determined. A balloon encasing a distal end of the fibre is inflated within the blood vessel to cause the balloon to limit flow of fluids within the vessel. Thermal radiation from the vessel is transmitted along the fibre to a detector Clearly, this method necessarily involves limiting flow of fluids within the blood vessel.

Stefanadis et al, in "Thermal Heterogeneity Within Human Atherosclerotic Coronary Arteries Detected in vivo", Circulation 1999,99,1965-1971, measured various temperatures of human coronary arteries in vivo.

Stefanadis et al determined the difference between temperatures in a control (background) region and temperatures at the surface of a region of interest (ROI). This work concluded that differences between ROI temperatures and background temperatures ranged from 1.55° C. in unstable angina patients to 2.60° C. in acute myocardial infarction patients. Mean differences between ROI and background temperatures were 0.683 in unstable angina patients and 1.472 in acute myocardial infarction patients. Mean values of these differences in stable angina patients were lower, in particular around 0.16° C., but this condition was not believed to be associated with the presence of vulnerable plaque. Indeed, there was no suggestion in this paper that any temperature differences were associated with vulnerable inflamed plaque.

This work was carried out using a thermography catheter The patients tested were those with severe lesions, in particular lesions more than 50% stenosed. This, combined with the particular catheter design used, had the effect that the catheter had to be wedged inside the lesions, severely restricting blood flow through the vessels. We believe that this severe restriction of blood flow led to artificially high temperature measurements

SUMMARY OF THE INVENTION

We now find that, contrary to these previous studies, in fact the thermal differences within the blood vessels of subjects whose arteries contain inflamed atherosclerotic plaque which may be vulnerable to rupture are much lower. In particular, we believe that the presence of inflamed atherosclerotic plaque can be foreshadowed by temperature differences from above zero to 0.39° C.

Therefore according to a first aspect of the invention we provide a method of diagnosing the presence of inflamed atherosclerotic plaque in a blood vessel of a subject, the method comprising:

providing a temperature detection device capable of detecting temperature at the inner vascular wall, introducing the temperature detection device into a blood vessel, determining a reference temperature value, measuring at least one first temperature value at the inner vascular wall, determining the difference between the first temperature value and the reference temperature value, and where the difference is above zero but not more than 0.39° C., diagnosing the presence of inflamed atherosclerotic plaque in the blood vessel.

In a second aspect of the invention we provide a method of determining whether a subject is in need of further investigation for the presence of inflamed atherosclerotic plaque, the method comprising:

provided a temperature detection device capable of detecting temperature at the inner vascular wall, introducing the temperature detection device into a blood vessel, determining a reference temperature value, measuring at least one first temperature value at the inner vascular wall, determining the difference between the first temperature value and the reference temperature value, and where the difference is above zero but not more than 0.39° C., determining that the subject requires further investigation for the presence of inflamed atherosclerotic plaque.

In a third aspect of the invention we provide a method of determining the location of an inflamed atherosclerotic plaque in a blood vessel of a subject, the method comprising:

providing a temperature detection device capable of detecting temperature at the inner vascular wall, introducing the temperature detection device into the blood vessel, determining a reference temperature value for the blood vessel, detecting at least one position on the inner vascular wall a temperature at the inner vascular wall above, but not more than 0 39° C. above, the reference temperature value, and determining that inflamed atherosclerotic plaque is situated at that position.

In a fourth aspect of the invention we provide a method of determining whether an atherosclerotic plaque in a blood vessel of a subject is an inflamed atherosclerotic plaque, the method comprising:

providing a temperature detection device capable of detecting temperature at the inner vascular wall, introducing the temperature detection device into the blood vessel, determining a reference temperature value for the blood vessel, detecting the temperature at the surface of the atherosclerotic plaque, determining the difference between the temperature at the surface of the atherosclerotic plaque and the reference temperature value, and if the difference is above zero but not more than 0.39° C., determining that the plaque is an inflamed atherosclerotic plaque.

We believe that the prior techniques described by Casscells et al and Stefanadis et al were such that, by restricting the flow of blood, they actively resulted in a change in the temperature measured in comparison with that which is present in vivo under normal conditions of blood flow for the subject. In the present invention we use a temperature measurement device which does not substantially inhibit blood flow in the subject A further benefit of such methods is that they may be applied to a wide variety of subjects without major concern that the measuring method itself will influence blood flow.

We find that when measurements are taken under conditions in which blood flow is not substantially inhibited, inflamed plaque can be associated with very low temperature differences, provided that they are above zero. We find that under conditions in which blood flow is not substantially inhibited then any variations in temperature along the blood vessel wall are generally "smoothed out" by the flow of blood along the vessel wall under these conditions only significant areas of temperature increase appear as measurable differences.

A further advantage of the realization that the presence of inflamed plaque is manifested by a much lower temperature differential than previously believed is that it is now possible to recognise at an early stage that subjects who exhibit these lower temperature differentials are at risk of plaque rupture Consequently monitoring and, if applicable, treatment may begin at an earlier stage and in subjects who would formerly have been believed not to be at risk of plaque rupture.

The invention relates to use of the novel finding discussed above in a variety of methods in certain aspects of the invention the method is a method of diagnosing subjects having inflamed atherosclerotic plaque and potentially at risk of plaque rupture. Such patients exhibit vascular temperature differences from above zero to 0.39° C. This finding can also be used in methods which do not diagnose definitively whether a subject has inflamed atherosclerotic plaque which is potentially vulnerable to rupture but distinguishes those subjects for whom further investigation would be beneficial.

The finding can be used to determine the position of inflamed atherosclerotic plaque by determining the position of a region of temperature elevated above zero and up to 0.39° C. thus locating inflamed atherosclerotic plaque in that position.

In a further aspect the finding can be used to determine whether a previously located plaque is inflamed and potentially vulnerable to rupture by determining whether its temperature is elevated by above zero but not more than 0.39° C.

The invention is concerned with detection and positioning of inflamed plaques. Such plaques are potentially unstable and consequently potentially vulnerable to rupture, erosion or ulceration.

When the existence and, if appropriate, the location of an inflamed plaque has been determined in a subject, then the subject can be further monitored and/or treated if appropriate.

Although we find that temperature differences above zero, that is those which are measurably different from the base value chosen as zero, can indicate the presence of an inflamed plaque, in general inflamed plaques usually exhibit temperature differences of at least 0.02° C. and preferably the value measured in all aspects of the invention is at least 0.02° C. We find that within the claimed range up to 0.39° C. temperature difference the greater values tend to indicate a greater degree of inflammation and thus greater potential for rupture etc. Thus we often find that a temperature difference of at least 0.1° C. is indicative of a plaque which is vulnerable to rupture and the invention is particularly valuable, in all aspects, when the temperature difference is at least 0.1° C.

In general temperature differences in the range of above zero to 0.39° C., in particular from 0.02 to 0.39° C., are generally indicative of a need to further investigate the subject for the presence of inflamed plaque, for instance as in the second aspect of the invention.

The subjects are living subjects, generally human subjects. Subjects may be patients already known to have a cardiovascular condition such as unstable angina or prior myocardial infarction. That is, the methods of the invention can be practised on subjects already known to have conditions which are associated with risk of vulnerable plaque rupture. In such patients the methods of the invention are particularly valuable for determination of the location of inflamed plaques and determination of whether a previously located plaque is inflamed and/or vulnerable to rupture.

However, the invention may also be practised on, and can be particularly valuable in, apparently healthy subjects who do not exhibit any symptoms of a cardiovascular condition In such subjects the invention can be used to diagnose the presence and, if desired, the location of inflamed plaque.

In all aspects of the invention it is essential that a temperature detection device is introduced into the blood vessel under investigation. The temperature detection device is capable of detecting the temperature at the inner wall of the blood vessel. Generally the temperature detection device is such that it is capable of obtaining temperature measurements without substantially restricting the flow of blood through the blood vessel.

By "without substantially restricting the flow of blood through the blood vessel" we mean that the temperature detection device does not reduce the blood flow velocity below a value at which it is capable of smoothing out local variations in temperature due to factors other than the presence of inflamed plaque. Preferably it does not restrict the flow of blood below the values discussed below.

In a human subject the normal range of blood flow velocity is from about 5 to about 40 cm/s, varying over the heart pulse cycle. In the invention the blood flow velocity is preferably at least 5 cm/s, more preferably at least 7 cm/s at all times throughout the cycle. That is, the temperature detection device is such that it does not restrict the flow of blood through the blood vessel to such an extent that velocity falls below this level at any time.

The average blood flow velocity can also be measured and in the invention is preferably at least 7 cm/s, more preferably at least 10 cm/s, more preferably at least 15 cm/S.

Generally the temperature detection device comprises sensors which transmit temperature data to a remote device for processing.

Particularly preferred devices are disclosed in our PCT publication WO 01/74263, the disclosure of which is incorporated herein by reference. In particular, the temperature detection device is preferably a thermography catheter apparatus. In particular it is preferably a vascular catheter apparatus for temperature measurement of vascular tissue, which comprises a flexible body, at least two thermal sensors mounted on resiliently biased projections depended from the body, and a carrier for transmitting temperature data at the vascular wall from the sensors to a remote device With the present invention, the vascular catheter apparatus, hereinafter referred to as a thermography catheter, is inserted into the artery to detect the temperature at the vascular wall. The temperature information is subsequently transferred via the carrier to a remote device where the wall temperature can be detected and recorded Generally, the thermography catheter comprises a plurality of co-axial lumen. Preferably, the thermography catheter comprises a central lumen adapted to be mounted on a standard angioplasty guide wire suitable for vascular intervention The apparatus is preferably based on the rapid-exchange (or monorail) system, although over-the-wire techniques are also envisaged. Preferably, outside the central lumen is located an intermediate lumen. Preferably, outside the intermediate lumen is mounted an external lumen, hereinafter referred to as a sheath. Preferably, at the distal tip of the apparatus is a guide member. Other lumen may be present and all the lumen may house components within themselves or between adjacent lumen.

The projections are preferably mounted on the central or intermediate lumen but may be attached to any lumen inside the sheath.

The central lumen may be formed from the standard catheter lumen materials, for example, nylon, PTFE, polyurethane, polycarbonate and silicones and mixtures thereof.

The intermediate lumen and the sheath are generally constructed from, but individually selected from, the standard catheter lumen materials discussed above The sheath is adapted to fit over the adjacent lumen housed inside the sheath and should be able to move relative to the adjacent lumen under the control of a remote device.

Preferably, the central and intermediate lumen are bound to one another and are not moveable relative to one another Preferably, the guide member is located at the extreme distal tip and is permanently mounted on the central lumen. Preferably, the guide member is formed from a material which minimises the possibility of damaging the vascular wall. For example, an elastic material is usually used to form the guide member. In particular, preferred materials for the guide member include nylon, PTFE, polyurethane, polycarbonate and silicones. The guide member is usually tapered towards the extreme distal tip and forms a general bullet or pear shape This enables easy manipulation of the catheter within the vascular tissue and minimises the possibility of potential damage to vascular tissue. The distal part, typically the last 20 cm or so, needs to be of sufficient flexibility for the thermography catheter to pass arterial angulations of at least 90° and up to 180° in vessels that may be as small as 2 mm, with a curvature radius that may be as low as 4 mm.

Preferably, the flexible body of the thermography catheter has a longitudinal axis and at least part of the projections are extensible radially from the longitudinal axis of the body. Generally, the projections nave an elongate shape, preferably having dimensions in the range of 2 mm to 15 mm, more preferably 3 to 7 mm in length. The projections preferably have a caliper of 0.3 mm to 5 mm, more preferably 0.5 mm to 3 mm.

A first end of the projection is preferably attached to the body, preferably the intermediate and/or the central lumen, while a second end comprises one or more sensors. The second end is preferably free, i.e, not attached to any of the lumen, and is adapted to be radially movable away from the central lumen Alternatively, the projection may be attached to a lumen at more than one position, for example at each end of the projection. Such a projection construction forms a loop. In such a case, the sensor is preferably located at the apex of the loop Two or more sensors, preferably two to ten sensors, more preferably two to six sensors may be utilised. Preferably, each sensor is mounted on a separate projection. In a particularly preferred example, four projections, each having a single sensor mounted thereon, are provided.

The sensors are preferably located on an outer face of the projection, relative the central lumen, i.e., facing the vascular tissue in use. Each sensor should preferably be located toward, or at the distal tip of the projection.

The projections need not be mounted in substantially the same circumferential plane of the thermography catheter body, but this configuration is preferred.

The projections preferably comprise a super-elastic material. Super-elasticity refers to the ability of certain metals to undergo large elastic deformation. Such compounds favorably exhibit features such as biocompatibility, kink resistance, constancy of stress, physiological compatibility, shape-memory deployment, dynamic interference, and fatigue resistance.

A large number of super-elastic materials may be utilised, however, Ni—Ti ternary alloys are preferred, particularly binary Ni—Ti with between 50.6 and 51.0 atomic percent nickel. While many metals exhibit super-elastic effects, Ni—Ti-based alloys appear to be best suited for deployment in the human body due to them being chemically and biologically compatible.

Preferably, the projection, when not restrained will adopt a deployed configuration in which a free end of the projection is extended away from the central lumen. In this deployed configuration, the projection is resiliently biased against the vascular wall in use, thus initiating contact between the sensor and said wall. This achieves an adequate thermal contact with the vascular wall, without substantially compromising blood flow.

In a particularly preferred embodiment of the invention, the elongate projection, when restrained, adopts a substantially straight shape, which lies substantially parallel to the longitudinal axis of the catheter body. In the deployed configuration, the projection adopts an arcuate shape along at least part of its length. In this embodiment, the gradient of the arcuate portion of the projection, with respect to the longitudinal axis of the catheter, increases as a function of distance along the projection from the end attached to the catheter body. Thus, the free end of the projection bends away from the catheter body. This particular embodiment allows the sensor-bearing end of the projections to more accurately and consistently follow the morphology of the vascular tissue. A stenosis usually involves a section of the wall being inflamed and thus protruding into the lumen of the blood vessel. Alternatively, a calcified plaque may have an irregular surface leading to it protruding into the lumen. Where an arcuate deployed projection is employed, the arc allows the sensor bearing tip to "reach around" to the trailing edge of a stenosed region as the catheter is moved along the vascular tissue. The arcuate nature of the projections also allows the temperature sensors to be located more directly and in closer contact to the vessel wall. The maximum gradient of the projection, with respect to the longitudinal axis of the catheter body is preferably less than 90°, more preferably less than 75°, more preferably less than 60°. In this particular embodiment, the arc of the projection preferably provides maximum possible contact angle between the projection and the vessel wall of less than 90°, more preferably less than 75°, more preferably less than 60°. This angle, while having a maximum deviation of less than 90°, is variable as a consequence of the compliant nature of the biased projection. This allows the projection to follow the vascular morphology.

Where an arcuate projection is provided, there may also be substantially straight portions of the projection along its length.

In an alternative example, the projections may be mounted to achieve a similar resiliently biased effect. For example, one method of achieving this would be to mount the projections on a spring, preferably a micro-spring, such that when unrestrained, the projection is extended against the vascular wall as discussed above.

The sensors may be any form of temperature sensor and are preferably selected from thermistors, thermocouples, infra red sensors and the like. Preferably, the sensors are thermistors. These are preferably metal alloys having low electrical impedance. Such thermistors prove extremely reliable regarding the relation between the temperature changes and resistance changes.

Generally, the sensors may be attached to the lumen by any means. Each sensor is preferably attached to the end of each projection permanently. For example, each projection may be attached to the lumen by glue, soldering, welding or may be formed integrally with the lumen Each sensor is connected to a carrier capable of transferring the information received from the vascular wall. The carrier preferably has a low impedance The carrier is in electrical connection with the proximal end of the device The carrier is preferably selected from nickel and copper wire.

Preferably, the thermography catheter comprises a radiopaque marker which aids in the location of the device by fluoroscopy during the method of the invention. More preferably, at least one sensor includes a marker so that it is discernible via fluoroscopy. Most preferably, individual sensors include different marker types, so that using fluoroscopy, the individual sensors can be identified and their spatial orientation and relative location to a desired part of the vessel wall thus clearly defined.

The distal tip may additionally comprise an ultrasound probe system that can give images of the arterial wall. This may be achieved by the incorporation to the distal catheter tip of a phased array of high-frequency ultrasonic crystals or a mechanical sector ultrasound element In this way, intravascular ultrasound (IVUS) images may be captured simultaneously with the temperature data. This is extremely useful for morphological data acquisition, correctly recognizing the area of interest and for accurate catheter positioning.

The proximal section of the thermography catheter incorporates a connector for coupling the temperature date signals to a remote device such as a personal computer. Preferably, the connector comprises n+1 female plugs to assure proper transmittance of the electrical voltage signal transmitted from the sensors, where n is the number of sensors These signals are transmitted along the wires from the sensors. The wires are preferably housed within the sheath and are preferably electrically isolated from the patient. Preferably, the wires are housed between the central lumen and the intermediate lumen, within the outer sheath. The n+1 female plugs are connected to n sensor wires and 1 common ground.

It is important to maintain electrical isolation between the electrical components and the patient In order to minimise the risk of fatigue (strain) failure caused by repeated shortening and lengthening of the electrical wires as the respective projections are deployed and retracted, whereby repeated compression and tensioning of the wire can cause a failure along the length of the wire and at the electrical connection to the thermistors and/or the sealed terminus between the central lumen and the intermediate lumen, causing an electrical short circuit in use, a preferred catheter apparatus comprises a body, at least one resiliently biased projection depended from the body, a sensor carried by the projection, and an electrical carrier connected to the sensor for transmitting data from the sensor to a remote device, wherein the electrical carrier is coiled.

In this aspect the catheter has one or more resiliently biased projections around which the electrical connection is coiled to reduce the strain at critical points where it is necessary to maintain a seal, and hence electrical isolation.

Preferably, the electrical carrier is coiled around the body of the projection.

Preferably, the pitch of the coil is arranged such that there are 5 to 10 turns per cm.

Preferably, a heat shrink wrapping is applied over at least a portion of the length of the projection. A heat shrink material is generally a polymeric material capable of being reduced in size upon application of heat. These are generally used in the form of a tube. Suitable materials include polyesters, PVC, polyolefins, PTFE and the like The preferred material is a polyester.

It is particularly important that substantial occlusion of the blood vessel is prevented. This is achieved by the preferred aspect of the present invention using the thermography catheters described because in a deployed configuration they do not substantially increase their radial cross sectional area beyond the radial cross sectional area of the apparatus in a retracted configuration.

Preferably, the ratio of the area of the cross-sectional profiles of the apparatus in the deployed to retracted configurations is in the range 4:1-1.1, preferably 3.1-1.25:1 more preferably 2.5:1-2:1, most preferably 1.75.1-1.25:1.

According to a preferred aspect of the present invention, the thermography catheter is used in combination with a pull-back device for manipulating a multiple lumen catheter. A particularly preferred pull-back device is disclosed in co-pending International patent application no PCT/EP02/09430, the contents of which are incorporated herein by reference.

In the invention a reference temperature value is determined and compared with at least one first temperature value at the inner wall of the blood vessel. Determination of the reference temperature value may be carried out either prior to or after introduction of the temperature detection device into a blood vessel.

The reference temperature value may be a predetermined value which is not measured during application of the method. For instance it may be a predetermined mean value of temperature at the inner vascular wall for the subject in question. It may for instance be a predetermined mean or minimum value of temperature at the inner vascular wall for a particular class of subjects (the class including the subject under investigation). For instance, the subject may have been subjected to measurement of temperature in the blood vessels on a previous occasion. Alternatively, mean or minimum values for normal blood vessel wall having no plaque, either for the subject being tested or for a particular class of subjects, may be used.

More usually, the reference temperature value is determined curing the application of the method. For instance, it may be the mean temperature value in the length of blood vessel under examination, as determined by taking a series of temperature values over that length during the application of the method. Alternatively, it may be the temperature value, eg an average value, for regions of blood vessels determined to be normal, i.e. having no plaque, also measured during application of the method.

Preferably, the reference temperature value measured during the application of the method is the minimum temperature value detected in the length of blood vessel under examination, or the temperature at regions having no plaque.

In the method at least one first temperature value at the inner wall of the blood vessel is measured. In practice it is preferred that more than one individual temperature value is measured. In particular at least five, preferably at least ten, more preferably at least twenty individual temperature values are measured at different locations along the length of a blood vessel under examination. Thus it is preferred that a series of individual temperature values at a series of locations is obtained.

The first temperature value to be compared with the reference temperature value is preferably the maximum of the individual temperature values detected along the length of blood vessel under examination. However, in sophisticated systems in which it is possible to establish temperatures which are temperatures at the surface of a plaque the first temperature value can be for instance a mean or maximum value for plaque surface temperatures.

Preferably, the method comprises obtaining a series of at least twenty individual temperature values from at least twenty different locations spaced from one another along the length of the blood vessel under examination and the reference temperature value is the minimum individual temperature value detected and the first temperature value is the maximum individual temperature value detected. Thus the difference determined in the method is the difference between the maximum and minimum detected temperatures.

According to the invention it is preferred that the temperature detection device, once introduced into the blood vessel under examination, is moved along the inside of the blood vessel so that temperature readings are taken along the length of the blood vessel under examination. Readings may be taken intermittently or substantially continuously.

It is possible simply to detect and record temperature data but it is preferred that the temperature data obtained from the temperature detection device is processed in such a way that it enables the operator of the method to determine which regions of the blood vessels contain inflamed plaque and which do not.

In particular, the temperature detection device such as a thermography catheter can be used to carry out a temperature scan along the length of the blood vessel under examination which can be used to produce a temperature map of the vascular tissue In a preferred aspect there is also used in the invention a computer program product which comprises computer executable instructions for manipulating image data and temperature data to generate an output in which the temperature data is mapped onto a corresponding position on an image where that temperature data was detected to provide an integrated graphical image output, wherein the temperature data is thermography data that represents surface temperature at a vascular wall, and the image data is representative of the vascular wall morphology.

According to a preferred aspect of the present invention, the method of obtaining the temperature data at the vascular wall comprises the steps of withdrawing a thermography catheter that senses vascular wall temperature over a predetermined length of the vascular tissue and processing the temperature data with reference to image data representative of the vascular wall morphology to provide an integrated graphical image output in which the temperature data is mapped onto a corresponding position on the image where that temperature data was detected Preferably the image data is one of angiogram image data or intravascular ultrasound image data of the same vascular wall.

Preferably, the integrated graphics image output is a two-dimensional representation of a target vessel morphology with a temperature profile of the target vessel wall overlaid Accordingly, it is then possible for the operator to visualise the temperature distribution in the blood vessel under examination. Preferably the temperature data is processed so that the graphical image output highlights regions in which the temperature difference is in the range from above zero to 0.39° C. This allows determination of the location of inflamed plaque.

In the invention a temperature difference above zero, preferably at least 0.02, up to 0.39° C. is indicative of inflamed plaque In particularly preferred methods a temperature difference of at least 0.05° C., more preferably at least 0.08° C., is taken as indicative of inflamed plaque. Generally we find that the presence of inflamed plaque is indicated by temperature differences not more than 0.3° C. and preferably not more than 0.25° C. In preferred processes determination of the presence of inflamed plaque or of need for further investigation can be effected where the temperature difference is 0.2° C. or below, preferably 0.15° C. or below, in particular 0.14° C. or below or 0.13° C. or below.

The method of the invention may be used to diagnose the presence of inflamed plaque in a blood vessel of a subject. Alternatively it may be used not to obtain a final diagnosis but to give a preliminary indication that the subject should be selected for further medical investigation for the presence of inflamed, potentially vulnerable, plaque The preferred vascular catheter apparatus (thermography catheter) for use in the present invention, subsequent to the identification and measurement of atherosclerotic plaque, may be used to treat an area identified as being at risk of rupture of said plaque Treatment may be effected by reinserting the catheter to a predetermined area of the vascular tissue. This reinsertion may be achieved in a controlled manner as the prior temperature measurement scan with the device may be used to produce a temperature map of the vascular tissue. This information may be stored in the remote device and can be used to relocate the area of risk. This procedure requires less contrast media to be infused into the patient than would normally be required in similar vascular interventional procedures as the position of the thermography catheter is known due to the data stored in the remote device. The pull-back device may then, under the control of a user, be used to drive the catheter back to, for example, the starting point of the temperature measurement or any point along the path of the temperature data acquisition, for further temperature measurements or alternative treatments of the vascular tissue.

For example, the catheter apparatus can then be used to treat the area by any of the usual therapeutic procedures, including localised delivery of a therapeutic agent, delivery of a stent, brachy therapy, ablation of selected tissue etc Thus the thermography catheter may additionally comprise angioplasty balloons or sleeves.

BRIEF DESCRIPTION OF THE DRAWINGS

Examples of the present invention will now be described in detail with reference to the accompanying drawings, in which:

FIG. 2 shows an enlarged partial section of an example of the distal tip of a thermography in accordance with the present invention in a deployed configuration;

FIG. 3 shows the catheter of FIG. 2 in a retracted configuration;

FIG. 4 is a flow diagram illustrating the steps involved with conducting intravascular catheterisation of a patient and the associated data capture and image processing; and, FIG. 5 shows an angiogram frame overlaid with a temperature profile.

FIG. 9 shows a representative temperature profile associated with a normal artery; and, FIG. 10 shows a representative temperature profile associated with an inflamed artery;

DETAILED DESCRIPTION

Figure 1:
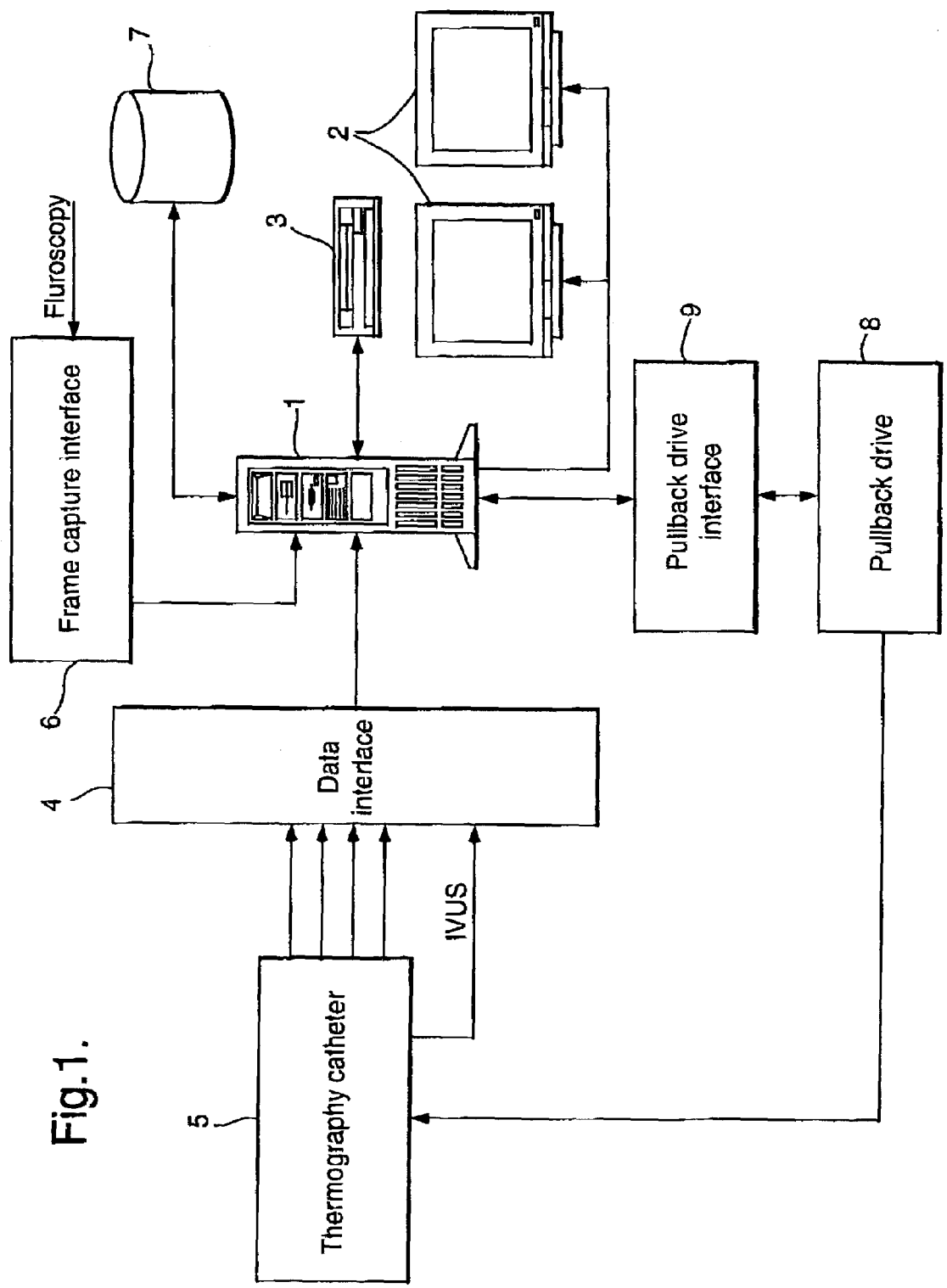
FIG. 1 shows a schematic diagram of a system for conducting vascular catheterisation of a patient.

FIG. 1 is a schematic diagram of a system for conducting vascular catheterisation of a patient.

The system includes a personal computer (PC) 1 that presents a graphical user interface (GUI) via a number of monitors 2. The user interface system is based on a Microsoft Windows™ platform. Multiple windows may be used to acquire/project data from/to the user. Although not shown, the PC can accept user inputs via a keyboard and mouse, or other pointing device, in the usual manner. The PC includes a number of data stores 7, which may be external, and a CD ROM reader/writer device 3

The PC is coupled via a data interface 4 to a thermography catheter 5, details of which will be described below. In this example, the thermography catheter 5 transmits four channels (one for each sensor) which are received by the data interface 4 An analogue temperature data signal on each channel is converted to a digital signal using an A/D converter within the data interface 4 at a user configured sampling rate of up to 2.5 KHz. Typically, the sampling rate would be set at around 25 to 50 Hz to reduce the quantity of data acquired.

The data interface 4 includes a multiplexer (not shown) that combines the four digital channels into a single time division multiplexed (TDM) signal This TDM signal is coupled to the PC over a PCI Pus. The data from each channel are written into an area of memory within the data store 7 reserved for that channel where they can subsequently be retrieved for data processing along with the corresponding time sequenced data from other channels and image data from other sources.

The temperature data from the thermography catheter 5 are introduced to the system software running on the PC using function calls Temperature data are input to the software as the actual voltage at the A/D hardware inputs, and therefore they have to be converted to temperature. A sensor data convert function handles this process The system is designed to be used in conjunction with a fluoroscopy x-ray apparatus and therefore includes a video frame capture interface 6 that couples fluoroscopy video data inputs to the PC via a PCI bus. Similarly, it can be used in conjunction with intravascular ultra-sound (IVUS) image data fed from the thermography catheter 5 (when provided with the appropriate hardware) The system software allocates sufficient memory area to the systems memory for this data, taking into account the current system configuration, for example sampling rate, recording time, and video frame size A memory handle hDib is used to map video data directly through the PCI bus from the video frame capture interface 6 to this allocated area in memory. hDib memory is divided into i equal chunks, each of a size equal to the frame capture interface frame-Puffer. Optionally, hDib [i] data can also be mapped to a memory area of a screen-video buffer, giving capability of live preview during recording. Each time the software records an x group of four (or more) temperature measurements, it prompts for a frame capture at hDib [x]. A user configuration file determines the ratio between temperature data fluoroscopy video frame capture Whilst in normal circumstances the thermography catheter 5 is inserted manually, it is intended that when performing vascular measurements the thermography catheter 5 is pulled back relative to a predetermined start position using an electro-mechanical pull-back drive 8 coupled to the body of the catheter. The pull-back drive 8 is controlled by the PC via a pull-back drive interface 9 The system software accesses user-defined configuration files to get the necessary information about controlling the systems automatic pullback interface 9. Data sampling rite, recording duration and pre-selected retraction rate are taken into consideration for adjusting the pull-back speed. The software routines control a D/A converter (not shown) that feeds the input of the pull-back interface 9 with an appropriate control voltage. The controlled pull-back process will be described in more detail below.

Temperature data plotting may be both on-line and/or off-line. In an on-line mode, the monitor presents a temperature/time-distance graph, where temperature is continuously plotted as connected dots. In an off-line mode, temperature data can be loaded from the data store 7 (or other media) and plotted on the screen graph. The user can scroll to different time/temperature locations, while several automated functions may be provided, for example auto minmax marking, colour coding of temperature an a bullseye graph colour thermal maps, and 3D temperature coding on a cylinder model In the latter case, an artificial colour 3D cylinder that represents the vessel is divided into splines equal to the temperature channels. The channel temperature is coded on each spline with colours varying from dark-blue (minimum temperature) to flashing-red (maximum temperature). The user can rotate the cylinder as he wishes in a virtual 3D world. The focus is set to the specific time/distance that corresponds to the mouse position on the screen temperature/time graph 3D position control is performed using multi cubic-bezier lines, where the curvation control points change in relation to the cylinders position in the virtual world. A separate window shows numeric details for the particular time/distance position. Video frame data from simultaneous fluoroscopy/IVUS are plotted as image frames in a separate window. By moving to a specific time/temperature position, the corresponding video frame is automatically projected. In this way, temperature and video frames are accurately synchronised.

The system software is designed to provide basic and advanced image processing functions for the captured fluoroscopy/IVUS video frames, such as filtering and on-screen measurement functions. The user can filter the captured frame to discard unwanted information while focusing on the desired one There are several auto-filter options as well as manual adjustment of the image curve In addition, the user can calibrate the system and proceed in performing on-screen measurements of both distances and/or areas. Automatic routines perform quantification of the measurements giving significant information on lesion characteristics The temperature can also be colour coded on the fluoroscopy frame, providing unique information about the correlation between temperature and morphology.

By using temperature data and video frame data, the system software uses advanced algorithms based on interpolation and fractal theory to plot a 3D reconstruction of the vessel under measurement with colour coding of temperature. The user can freely move the virtual camera inside the reconstructed vessel in 360°, and/or fly-through the vessel. 2D reconstructions are also provided. Temperature data can be processed on the basis of mean temperature, or on a channel-by-channel basis.

FIGS. 2 and 3 show an example of the distal tip of a thermography catheter incorporating sensors 10 mounted circumferentially about a central lumen 14. In this example, four sensors 10 are mounted on resiliently biased projections 11 circumferentially about the central lumen at 90° intervals, although only one sensor is shown here for the sake of clarity. The projections 11 are made of NiTinol The figures clearly show the deployed configuration projection adopting an arcuate shape along its length, with the gradient of the projection, with respect to the longitudinal axis of the catheter, increasing as a function of distance along the projection from the end attached to the catheter body.

The sensors 10 are NTC thermistors. Such thermistors prove extremely reliable regarding the relation between the temperature changes and resistance changes. An NTC thermistor having a 30 KΩ impedance at 25° C. typically maintains linearity between 35° C. and 45° C., at a resolution of 0.01° C.-0.1° C.

The construction of the thermistors 10 are that of two rectangular plates with a metal alloy oxide in the centre. The thermistor has dimensions in the range of 0.25 mm-5 mm, and a caliper less than 1 mm.

Each thermistor 10 is attached to the end of each projection 11 by bonding with an thermally conducting epoxy glue 12. Each thermistor 10 is connected to an insulated bifilar wire 13. The wire 13 has a low impedance and is constructed from nickel and/or copper. This wire provides an electrical connection with the proximal end of the device (not shown).

As shown in the Figures, the wire 13 is coiled around the length of the projection 11 This feature has the effect of substantially eliminating strain when the projection 11 flexes. The pitch of the coil is typically arranged to be such that there are 5 to 10 turns over a length of 10 mm. As will be described below, a neat shrink wrapping 15 is applied over the projection 11 to prevent damage to the wire 13 during retraction and replacement of an outer sheath 16. The neat shrink wrapping also provides an additional degree of electrical isolation.

To assemble a projection, a NiTinol arm is first pretreated by placing it in a bending tool and heating to around 700° C. to impart a bend in the arm The NiTinol arm is then held straight in a chuck and a thermistor/bifilar wire assembly is attached to a free end of the arm using a UV cure adhesive. The wire 13 is then spun around the length of the NiTinol arm. Finally, the neat shrink wrapping 15 is placed over the length of the NiTinol arm to a point just beyond that of the thermistor. In tis example, the heat shrink wrapping is supplied as a polyester tube that is cut to length An epoxy resin is then injected into the end of the tube The assembly is subsequently heat treated to shrink the tube and set the epoxy resin. The heat shrink wrapping is then trimmed back to expose at least part of the epoxy resin coated thermistor, while maintaining electrical isolation of the bifilar wires. After neat treatment, the heat shrink has a wall thickness of around 10 μm.

As shown in the Figures, the thermography catheter is mounted on an angioplasty guide wire (not shown) which runs through the central lumen 14 and a guide member 17 which defines the tip of the thermography catheter.

In use, the apparatus may be actuated between a non-wall-temperature sensing configuration and a temperature sensing configuration. The non-temperature sensing configuration is hereinafter referred to as the retracted configuration. The temperature sensing configuration is hereinafter referred to as the deployed configuration. An example of the deployed configuration is shown in FIG. 2. An example of the retracted configuration is shown in FIG. 3

In the retracted configuration, the sheath 16 encompasses the projections 11 so that they are constrained to lie parallel to the longitudinal axis of the catheter and therefore cannot take up a deployed position. The sheath 16 extends as far as the rear end of the guide member 17 but does not overlap the guide member. This minimises any protrusions from the thermography catheter which could lead to damage of the vascular wall. This is particularly important where a vessel is angulated or there is bifurcation of the vessel. Such features lead to bending of the thermography catheter and would emphasise any protrusions. Hence, in this example the sheath 16 and the guide member 17 present a smooth profile when adjacent to one another in the retracted configuration.

To adopt the deployed configuration, the sheath 16 is withdrawn away from the extreme distal tip i.e., away from the guide member 17, towards the proximal section, to expose the projections 11. When the sheath 16 is withdrawn to the extent shown in FIG. 2, the resiliently biased projections 11 take up the deployed configuration. It should be noted that the sheath is controlled from the proximal end of the apparatus and is not shown in its entirety in the Figures.

The projections 11 individually extend a certain distance (r) away from the longitudinal axis of the catheter. In the deployed configuration, r has a value in the range of 2-4 mm. However, r is not fixed and varies with the diameter of the vascular tissue being measured due to the flexibility of the projections 11.

Different diameter catheters may be used for different diameters of vascular tissue. However, as it is desirable to minimize the diameter of catheters in all interventional vascular treatments, it is desirable to adapt the length of the projections and/or the angle to which the projections may extend away from the central lumen depending on the dimensions of the vascular tissue being measured rather than increasing catheter body dimensions Thus, the projections for a large blood vessel, for example 8 mm diameter, will generally require a length of projection in the range of 5 mm to 10 mm. Smaller diameter vascular tissue, for example 2.5 mm diameter, will generally require a length of projection in the range of 2 mm to 6 mm. Typically, the ratio of the area of the cross-sectional profiles of the apparatus in the deployed to retracted configurations is up to 4:1.

The thermography catheter includes a valve system (not shown) allowing the annular gap between the sheath and the intermediate lumen to be flushed in an adequate way, thus minimising the possibility of air bubbles or debris within the sheath Such a valve is constructed to enable engagement by a 2 mm, 5 mm, or 10 mm, 6° luer syringe. The thermography catheter may be flushed with a suitable fluid such as saline. When flushing the catheter, fluid should exit via the distal tip of the catheter, indicating proper flushing of the sheath In addition, the catheter includes a female luer fitting (not shown) attached to the proximal end of the central lumen, to enable the central lumen to be flushed in a similar way to the sheath.

With reference to FIG. 4, in use, the sequence of events begins with the insertion of a guiding catheter into the area of general interest (step 100), for example the cardiac region. Where, for example, the coronary arteries are to be examined, the guiding catheter is inserted so that it is in or adjacent to the opening of the coronary arteries. An angioplasty guide wire is then inserted into the coronary artery, past the point of specific interest (step 110). The guide wire is usually inserted with the aid of standard fluroscopic techniques, as is the guiding catheter. Once the guiding catheter and guide wire are in position, the thermography catheter of the present invention is maneuvered over the guide wire to a position beyond the specific area of interest in the coronary artery (step 120) with the aid of fluoroscopy.

An angiogram is taken (step 130) to assess the position of the thermography catheter in the vascular tissue. This image is saved and the position of the thermography catheter is marked on the image so as to define a starting point for the controlled pull-back step.

The guiding catheter is then locked in position and both the sheath and the lumen housed in the sheath are locked to mounts on the pull-back device. The sheath is then retracted to allow the projections to adopt the deployed configuration. Controlled pull-back of the thermography catheter then takes place (step 140). The pull-back takes place at a constant speed and is controllable by the user. Pull-back typically takes place at speeds of 0.1 to 2 mm in divisions of 0.1 mm or so The pull-back takes place over a distance of the vascular tissue being measured. Temperature readings may be taken intermittently or substantially continuously. The data transmitted by the sensors from the vascular wall is captured for data and image processing (step 150) together with a fluoroscopy/IVUS image frame.

As the thermography catheter is withdrawn inside the artery, the projections automatically adjust their angle following the wall's morphology without losing the desired thermal contact. The result is that the thermal contact between the sensors and the wall is continuously maintained, even when the catheter is crossing very irregular plaque formations.

Once the pull-back has been completed relative movement between the sheath and the intermediate lumen places the sensors in the retracted configuration. This restores the original smooth profile of the thermography catheter.

As mentioned above, the system software has the capability to capture image-frames that come from standard fluoroscopy or IVUS devices simultaneously with temperature Spatial data that come from fluoroscopy/IVUS are combined by the software with temperature data. This is done as follows: Before the thermography procedure starts, and while the thermography catheter is still out of the target vessel, the user records the fluoroscopy-tube/bed position and records a video frame during injection of contrast media. The vessel is opacified, and the image is stored and projected on one of the system monitors. The user calibrates the pixel/mm relation by using the guiding catheter as a known reference so that distances in mm can subsequently be estimated accurately on the monitor.

Figure 5:
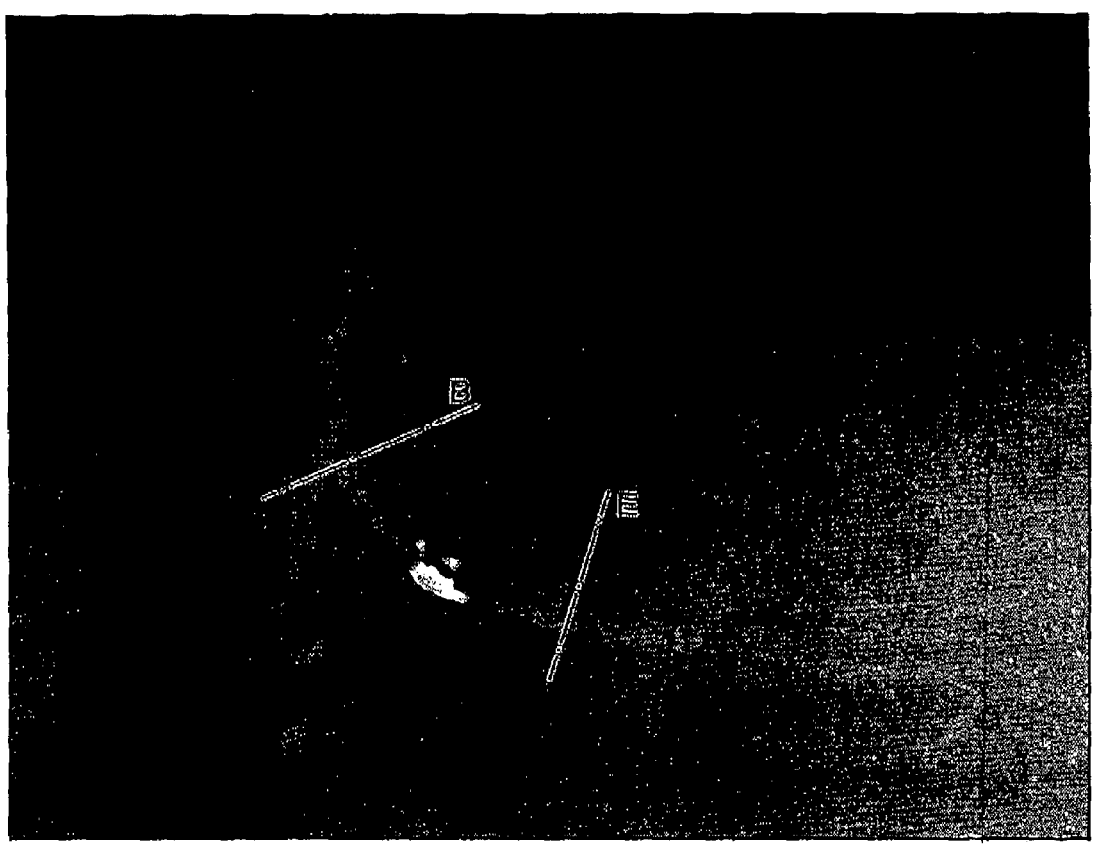

As shown in FIG. 5, the user then marks the beginning and ending of the area of interest (points B and E) by clicking on them using the mouse: in return, the software marks these points on the monitor by arrows or lines. The user then positions the thermography catheter in the target vessel by pushing it forward on the guide wire until the fluoroscopic marker on the thermography catheter passes point E over a few mm; while watching the system's monitor, the thermal sensors are then deployed and the user manually pulls the thermography catheter back gently until the fluoroscopic marker overlaps exactly on point E. The software then instructs the automatic pull-back device to pull back the thermography catheter over the length of the BE curve within the vessel.

The software then performs auto-border detection on the BE area of the fluoroscopy video frame using a photoluminescence technique, and temperature is subsequently coded in the atherosclerotic plaque outline as RGB color degradation from dark-blue (0,0,255) corresponding to the minimum detected temperature, to flashing red (255,0,0) corresponding to the maximum detected temperature. A reference color map may be provided, and by moving the mouse cursor inside the BE area, temperature values may also automatically be provided in a numeric format.

Figure 6:
FIG. 6 shows a single IVUS image frame overlaid with a temperature profile.
Figure 7:
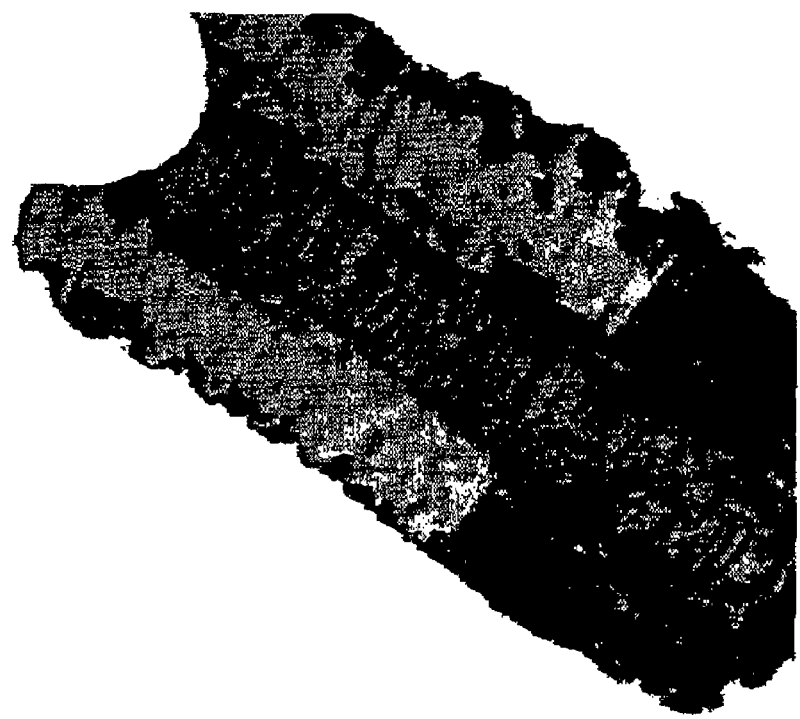
FIG. 7 shows a 3D section of a target vessel constructed using a series of IVUS images (without temperature mapping)
Figure 8:
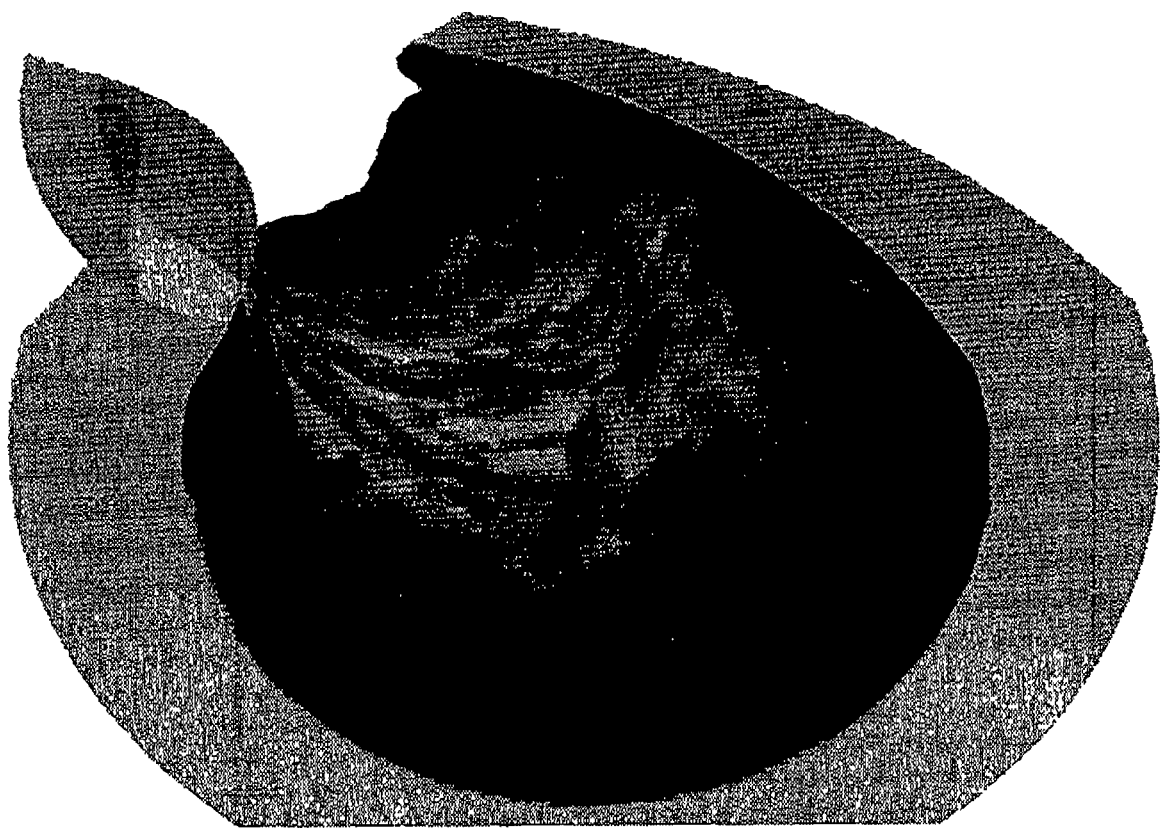
FIG. 8 shows an IVUS as a 3D section with temperature mapping overlaid.

FIG. 6 Shows the same image processing as applied to a single IVUS image frame for a section of the target vessel. FIG. 7 shows a 3D section of a target vessel constructed using a series of IVUS images (without temperature mapping) As shown in FIG. 8, a number of IVUS images can be processed to provide a 3D representation of the temperature profile/morphology over a length of the target vessel. This is a actual image of the artery of a patient having an unstable coronary syndrome FIGS. 9 and 10 show temperature profiles obtained in a normal artery having substantially no inflamed plaque and an artery known to contain inflamed plaque, respectively, obtained by continuous sampling of temperatures using a thermography catheter having 4 sensors. The values obtained for the 4 different sensors are shown in the figures The zero value is the mean value for the normal artery.

EXAMPLES

The examples below show the results of obtaining a series of individual temperature measurements in the blood vessels of a series of patients. Measurements were carried out using a thermography catheter as described above in FIGS. 2 and 3 Table 1 below shows the heterogeneity measured in the blood vessel, namely the difference between the lowest individual temperature value (reference temperature value) and the highest individual temperature value (first temperature value). These values are measured as deviation from the temperature at non-atherosclerotic ("normal") vessel wall. All values are in degrees centigrade (° C.).

TABLE 1

| Patient | Highest value (° C.) | Lowest value (° C.) | Heterogeneity (° C.) |
|---|---|---|---|
| 1 | 0.06 | −0.03 | 0.09 |
| 2 | 0.03 | −0.01 | 0.04 |
| 3 | 0.04 | −0.01 | 0.05 |
| 4 | 0.03 | −0.02 | 0.05 |
| 5 | 0.02 | −0.01 | 0.03 |
| 6 | 0.02 | −0.03 | 0.05 |
| 7 | 0.02 | −0.07 | 0.09 |
| 8 | 0.16 | −0.02 | 0.18 |
| 9 | 0.05 | −0.02 | 0.07 |
| 10 | 0.02 | 0 | 0.02 |
| 11 | 0.07 | 0.01 | 0.06 |
| 12 | 0.04 | −0.09 | 0.13 |
| 13 | 0.01 | −0.02 | 0.03 |
| 14 | 0.02 | −0.01 | 0.03 |
| 15 | 0.03 | −0.02 | 0.05 |

It is believed that the results from patients 1 to 15 are all indicative of the likely presence of inflamed plaque, particular patients 8 an 12 Further results are shown in Table 2 below.

TABLE 2

| Patient | Highest value (° C.) | Lowest value (° C.) | heterogeneity (° C.) |
|---|---|---|---|
| 16 | 0.02 | −0.12 | 0.14 |
| 17 | 0.03 | −0.11 | 0.14 |
| 18 | 0.02 | −0.09 | 0.11 |
| 19 | 0.07 | −0.01 | 0.08 |
| 20 | 0.02 | −0.06 | 0.08 |
| 21 | 0.01 | −0.01 | 0.08 |

From these results we believe that patients 16 to 18 are most at risk of plaque rupture.

The invention claimed is:

1. A method of diagnosing the presence of inflamed atherosclerotic plaque in a blood vessel of a subject, the method comprising:
    providing a temperature detection device which detects temperature at the inner vascular wall,
    introducing the temperature detection device into a blood vessel,
    determining a reference temperature value,
    measuring at least one first temperature value at the inner vascular wall, determining the difference between the first temperature value and the reference temperature value, and
    diagnosing the presence of inflamed atherosclerotic plaque in the blood vessel where the difference is above zero but not more than 0.14° C.

2. A method of determining whether a subject is in need of further investigation for the presence of inflamed atherosclerotic plaque, the method comprising:
    providing a temperature detection device which detects temperature at the inner vascular wall,
    introducing the temperature detection device into a blood vessel,
    determining a reference temperature value,
    measuring at least one first temperature value at the inner vascular wall, determining the difference between the first temperature value and the reference temperature value, and
    determining that the subject requires further investigation for the presence of inflamed atherosclerotic plaque where the difference is above zero but not more than 0.14° C.

3. A method of determining the location of an inflamed atherosclerotic plaque in a blood vessel of a subject, the method comprising:
    providing a temperature detection device which detects temperature at the inner vascular wall,
    introducing the temperature detection device into the blood vessel,
    determining a reference temperature value for the blood vessel,
    detecting at least one position on the inner vascular wall a temperature at the inner vascular wall above, but not more than 0.14° C. above the reference temperature value, and
    determining that the inflamed atherosclerotic plaque is situated at that position.

4. A method of determining whether an atherosclerotic plaque in a blood vessel of a subject is an inflamed atherosclerotic plaque, the method comprising:
    providing a temperature detection device which detects temperature at the inner vascular wall,
    introducing the temperature detection device into the blood vessel,
    determining a reference temperature value for the blood vessel,
    detecting the temperature at the surface of the atherosclerotic plaque,
    determining the difference between the temperature at the surface of the atherosclerotic plaque and the reference temperature value, and
    determining that the plaque is an inflamed atherosclerotic plaque if the difference is above zero but not more than 0.14° C.

* * * * *